US010085698B2

(12) United States Patent
Fan et al.

(10) Patent No.: US 10,085,698 B2
(45) Date of Patent: Oct. 2, 2018

(54) METHODS AND SYSTEMS FOR AUTOMATED TUBE CURRENT MODULATION

(71) Applicant: General Electric Company, Schenectady, NY (US)

(72) Inventors: Jiahua Fan, New Berlin, WI (US); Xiaoyu Tian, Durham, NC (US); Dominic Joseph Crotty, Waukesha, WI (US)

(73) Assignee: Genereal Electric Company, Schenectady, NY (US)

( * ) Notice: Subject to any disclaimer, the term of this patent is extended or adjusted under 35 U.S.C. 154(b) by 285 days.

(21) Appl. No.: 15/006,840

(22) Filed: Jan. 26, 2016

(65) Prior Publication Data
US 2017/0209105 A1   Jul. 27, 2017

(51) Int. Cl.
*A61B 6/03*   (2006.01)
*H05G 1/34*   (2006.01)
*A61B 6/00*   (2006.01)

(52) U.S. Cl.
CPC .............. *A61B 6/032* (2013.01); *A61B 6/461* (2013.01); *A61B 6/54* (2013.01); *A61B 6/542* (2013.01); *A61B 6/544* (2013.01); *A61B 6/545* (2013.01); *H05G 1/34* (2013.01)

(58) Field of Classification Search
CPC ........... A61B 6/032; A61B 6/54; A61B 6/542; A61B 6/544; A61B 6/545; H05G 1/34
USPC ........................................... 378/16, 108–110
See application file for complete search history.

(56) References Cited

U.S. PATENT DOCUMENTS

| | | | | | |
|---|---|---|---|---|---|
| 5,379,333 | A | * | 1/1995 | Toth | A61B 6/032 378/108 |
| 5,400,378 | A | * | 3/1995 | Toth | A61B 6/032 378/108 |
| 5,450,462 | A | * | 9/1995 | Toth | A61B 6/032 378/108 |
| 5,485,494 | A | * | 1/1996 | Williams | A61B 6/032 378/110 |
| 5,625,662 | A | * | 4/1997 | Toth | H05G 1/26 378/108 |

(Continued)

OTHER PUBLICATIONS

Wang, S. et al., "An Automated DICOM Database Capable of Arbitrary Data Mining (Including Radiation Dose Indicators) for Quality Monitoring," Journal of Digital Imaging, vol. 24, No. 2, Apr. 2011, Published Online Sep. 8, 2010, 11 pages.

(Continued)

*Primary Examiner* — Allen C. Ho
(74) *Attorney, Agent, or Firm* — McCoy Russell LLP (57) ABSTRACT

Methods and systems are provided for automated tube current modulation (ATCM). In one embodiment, a method for an imaging system comprises: calculating a desired dose level based on a clinical task, a size of a subject to be scanned, and an image quality level; generating a scan protocol based on a relation between the image quality level and at least one characteristic of the imaging system; and performing a scan of the subject at the desired dose level and according to the generated scan protocol. In this way, ATCM can be optimized based on elements that impact image quality such as the clinical task, the physical characteristics of the imaging system, the individual patient, and the reader's preference.

20 Claims, 5 Drawing Sheets

(56) References Cited

U.S. PATENT DOCUMENTS

| | | | | |
|---|---|---|---|---|
| 5,696,807 A * | 12/1997 | Hsieh | A61B 6/032 | 378/109 |
| 5,822,393 A * | 10/1998 | Popescu | A61B 6/032 | 378/108 |
| 5,867,555 A * | 2/1999 | Popescu | A61B 6/032 | 378/16 |
| 6,385,280 B1 * | 5/2002 | Bittl | A61B 6/032 | 378/106 |
| 6,404,844 B1 * | 6/2002 | Horiuchi | A61B 6/032 | 378/16 |
| 6,490,337 B1 * | 12/2002 | Nagaoka | A61B 6/032 | 378/16 |
| 6,507,639 B1 * | 1/2003 | Popescu | A61B 6/032 | 378/108 |
| 6,744,846 B2 * | 6/2004 | Popescu | A61B 6/032 | 378/16 |
| 6,754,301 B2 * | 6/2004 | Horiuchi | A61B 6/032 | 378/16 |
| 6,775,352 B2 * | 8/2004 | Toth | A61B 6/032 | 378/101 |
| 6,904,127 B2 * | 6/2005 | Toth | A61B 6/032 | 378/108 |
| 6,956,929 B2 | 10/2005 | Wolf et al. | | |
| 6,987,828 B2 * | 1/2006 | Horiuchi | G01N 23/046 | 378/108 |
| 6,990,171 B2 * | 1/2006 | Toth | A61B 6/032 | 378/158 |
| 6,990,172 B2 * | 1/2006 | Toth | A61B 6/032 | 378/109 |
| 7,039,163 B2 * | 5/2006 | Popescu | A61B 6/032 | 378/109 |
| 7,042,977 B2 * | 5/2006 | Dafni | A61B 6/032 | 378/16 |
| 7,068,750 B2 * | 6/2006 | Toth | A61B 6/032 | 378/156 |
| 7,103,139 B2 * | 9/2006 | Nagaoka | A61B 6/032 | 378/16 |
| 7,106,824 B2 * | 9/2006 | Kazama | A61B 6/032 | 378/110 |
| 7,142,630 B2 * | 11/2006 | Suzuki | A61B 6/032 | 378/16 |
| 7,145,982 B2 * | 12/2006 | Ikeda | A61B 6/032 | 378/16 |
| 7,203,270 B2 * | 4/2007 | Okumura | A61B 6/032 | 378/109 |
| 7,215,733 B2 * | 5/2007 | Nabatame | A61B 6/032 | 378/110 |
| 7,277,523 B2 * | 10/2007 | Mattson | A61B 6/032 | 378/15 |
| 7,336,762 B2 * | 2/2008 | Seto | A61B 6/032 | 378/110 |
| 7,391,843 B2 * | 6/2008 | Toth | A61B 6/488 | 378/16 |
| 7,558,364 B2 * | 7/2009 | Lin | A61B 6/032 | 378/16 |
| 7,558,365 B2 * | 7/2009 | Wang | A61B 6/032 | 378/16 |
| 7,587,023 B2 | 9/2009 | Hur | | |
| 7,602,880 B2 * | 10/2009 | Hirokawa | A61B 6/032 | 378/108 |
| 7,620,142 B1 * | 11/2009 | Toth | A61B 6/032 | 378/108 |
| 7,636,416 B2 * | 12/2009 | Miyazaki | A61B 6/542 | 378/108 |
| 7,639,776 B2 * | 12/2009 | Gohno | A61B 6/032 | 378/109 |
| 7,715,522 B2 * | 5/2010 | Goto | A61B 6/032 | 378/16 |
| 7,734,006 B2 * | 6/2010 | Miyazaki | A61B 6/542 | 378/101 |
| 7,756,243 B2 * | 7/2010 | Gohno | A61B 6/032 | 378/16 |
| 7,813,471 B2 * | 10/2010 | Hirokawa | A61B 6/032 | 378/4 |
| 7,945,013 B2 * | 5/2011 | Goto | A61B 5/4869 | 378/16 |
| 7,983,457 B2 * | 7/2011 | Toth | A61B 6/032 | 378/16 |
| 8,175,217 B2 * | 5/2012 | Sugaya | A61B 6/032 | 378/16 |
| 8,649,480 B2 * | 2/2014 | Yoshida | A61B 6/032 | 378/16 |
| 8,699,658 B2 * | 4/2014 | Yu | A61B 6/032 | 378/16 |
| 8,744,039 B2 * | 6/2014 | Hirokawa | A61B 6/032 | 378/108 |
| 8,744,040 B2 * | 6/2014 | Sugaya | A61B 6/032 | 378/16 |
| 8,798,228 B2 | 8/2014 | Chandrashekarappa et al. | | |
| 8,848,860 B2 * | 9/2014 | Yazaki | A61B 6/488 | 378/16 |
| 9,226,719 B2 * | 1/2016 | Goto | A61B 6/032 | |
| 9,254,107 B2 * | 2/2016 | Sugaya | A61B 6/032 | |
| 9,332,953 B2 * | 5/2016 | Suzuki | A61B 6/488 | |
| 9,592,022 B2 * | 3/2017 | Larson | A61B 6/032 | |
| 9,592,023 B2 * | 3/2017 | Tanaka | A61B 6/032 | |
| 9,870,610 B2 * | 1/2018 | Makifuchi | G06T 7/0002 | |
| 9,968,307 B2 * | 5/2018 | Stevens | A61B 6/032 | |
| 2014/0270053 A1 | 9/2014 | Larson | | |
| 2015/0201895 A1 | 7/2015 | Suzuki | | |

OTHER PUBLICATIONS

Ikota, I. et al., "Estimating Patient Dose from X-ray Tube Output Metrics: Automated Measurement of Patient Size from CT Images Enables Large-scale Size-specific Dose Estimates," Radiology, vol. 270, No. 2, Feb. 2014, Published Online Oct. 28, 2013, 9 pages.

* cited by examiner

METHODS AND SYSTEMS FOR AUTOMATED TUBE CURRENT MODULATION

FIELD

Embodiments of the subject matter disclosed herein relate to non-invasive diagnostic imaging, and more particularly, to automated tube current modulation in computed tomography (CT) imaging.

BACKGROUND

Non-invasive imaging technologies allow images of the internal structures of a patient or object to be obtained without performing an invasive procedure on the patient or object. In particular, technologies such as computed tomography (CT) use various physical principals, such as the differential transmission of x-rays through the target volume, to acquire image data and to construct tomographic images (e.g., three-dimensional representations of the interior of the human body or of other imaged structures).

Modern CT systems use a technique known as automated tube current modulation (ATCM) to set the dose operating point for an optimized performance between image quality and radiation dose. Traditionally, ATCM generally adapts the tube current to maintain a constant signal at the image detectors, which results in a constant noise across the whole reconstructed volume. Such a strategy, while generally automated, simply relies on noise (image pixel standard deviation) as a universal image quality index.

However, several key elements of the diagnostic procedure, such as system resolution, noise texture, and task-related information are not effectively modeled when performing ATCM based solely on image noise. Besides, since pixel noise is utilized as the only constraint, the final targeted image quality level is usually based on radiologists' subjective preference of image noise level, which does not offer flexibility towards optimized performance of the diagnostic procedure for different clinical tasks and different radiologists.

BRIEF DESCRIPTION

In one embodiment, a method for an imaging system comprises: calculating a desired dose level based on a clinical task, a size of a subject to be scanned, and an image quality level; generating a scan protocol based on a relation between the image quality level and at least one characteristic of the imaging system; and performing a scan of the subject at the desired dose level and according to the generated scan protocol. In this way, ATCM can be further optimized based on additional elements that affect image quality such as the clinical task and the physical characteristics of the imaging system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
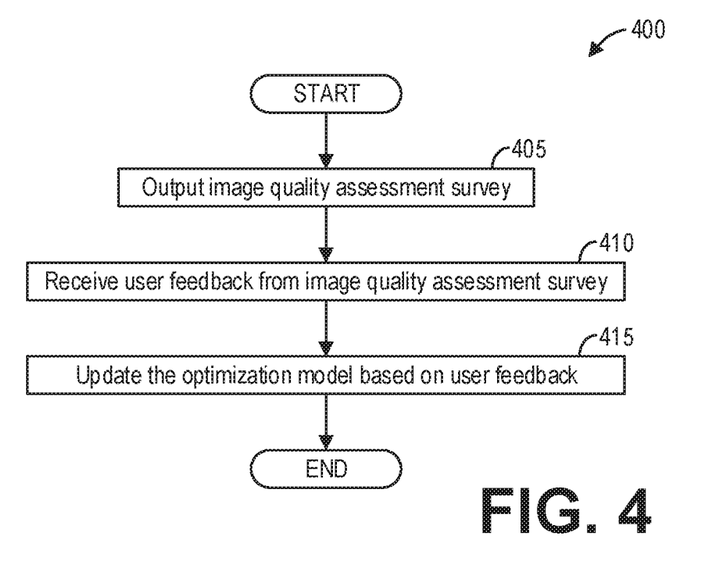
FIG. 4 shows a high-level flow chart illustrating an example method for adapting an optimization model according to an embodiment of the invention.
Figure 5:
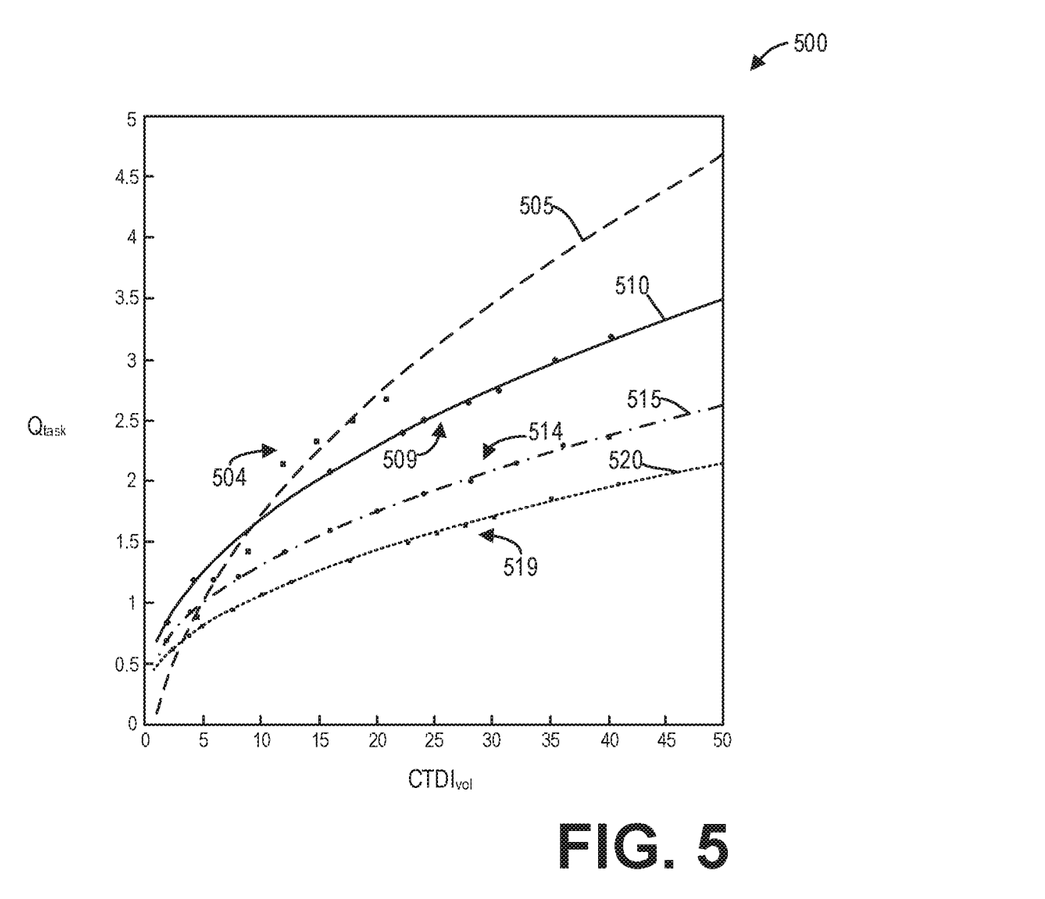
FIG. 5 shows a graph illustrating an image quality metric as a function of dose level for a single patient at different tube peak kilovoltages according to an embodiment of the invention.
Figure 6:
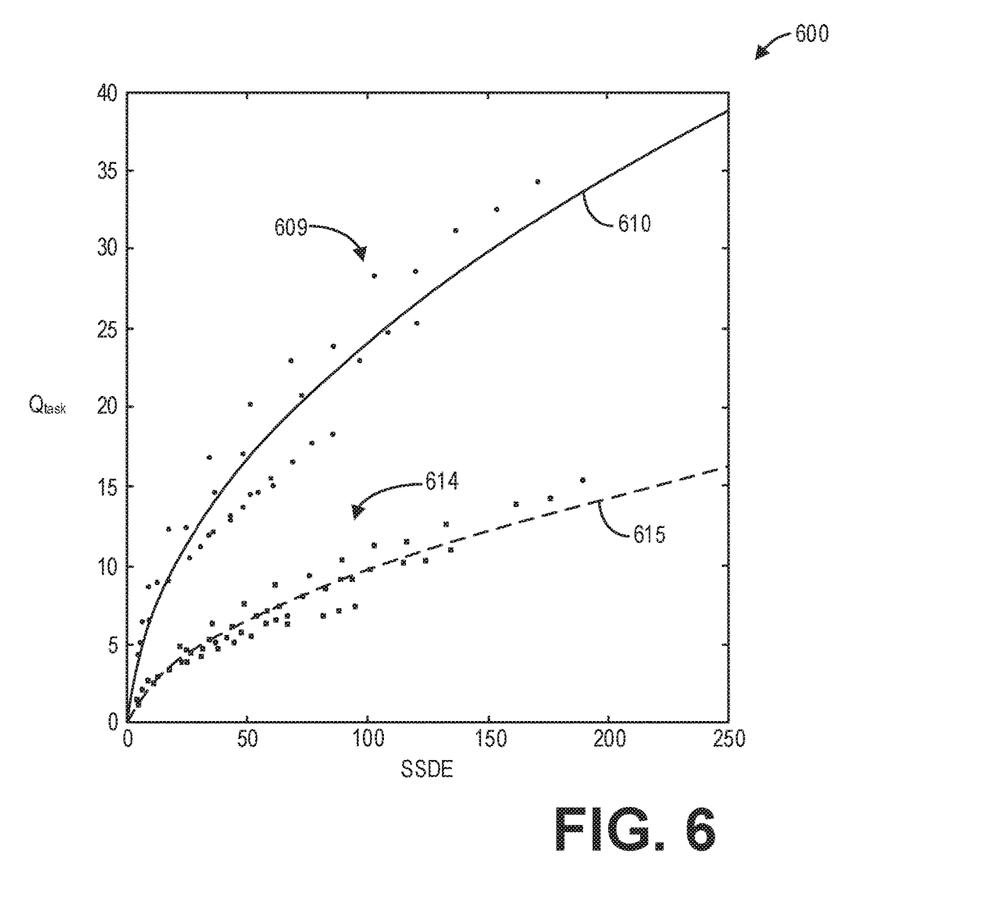
FIG. 6 shows a graph illustrating an image quality metric as a function of dose level for patients of different sizes according to an embodiment of the invention.

The following description relates to various embodiments of medical imaging systems. In particular, methods and systems are provided for automated tube current modulation. An example of a computed tomography (CT) imaging system that may be used to acquire images processed in accordance with the present techniques is provided in FIGS. 1 and 2. A method for ATCM, such as the method depicted in FIG. 3, may determine an optimal dose level and an optimal scan protocol based on characteristics of a particular patient being scanned, characteristics of the particular imaging system being used to scan the patient, the particular clinical task, and a targeted image quality level. As depicted in FIG. 4, machine learning techniques may be used to update an ATCM optimization model based on user feedback regarding images reconstructed according to the method of FIG. 3. FIGS. 5 and 6 depict example relationships between an image quality index and different dose indices.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

As used herein, the phrase "pixel" also includes embodiments of the invention where the data is represented by a "voxel." Thus, both the terms "pixel" and "voxel" may be used interchangeably herein.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on, for example, a cathode ray tube display.

Figure 1:
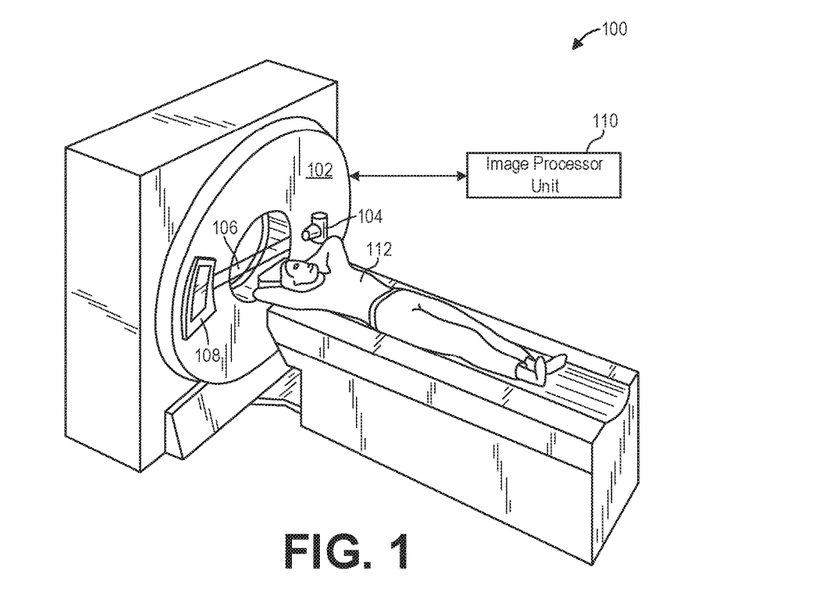
FIG. 1 shows a pictorial view of an imaging system according to an embodiment of the invention.

FIG. 1 illustrates an exemplary CT system 100 configured to allow fast and iterative image reconstruction. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the x-ray radiation source 104 is configured to project the beam of x-ray radiation 106 towards a detector array 108 positioned on the opposite side of the gantry 102. Although FIG. 1 depicts only a single x-ray radiation source 104, in certain embodiments, multiple radiation sources may be employed to project a plurality of beams of x-ray radiation 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as adaptive statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
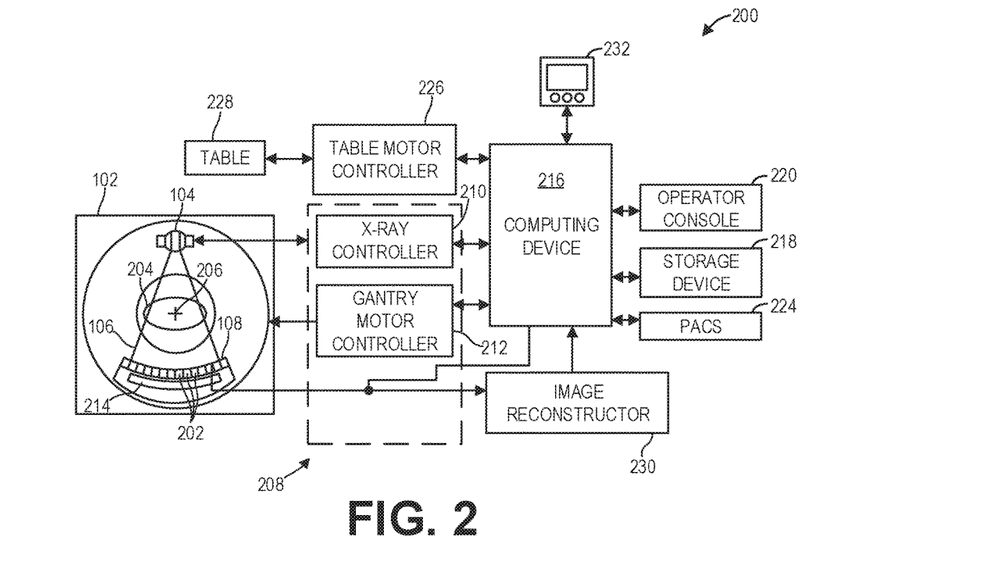
FIG. 2 shows a block schematic diagram of an exemplary imaging system according to an embodiment of the invention.

FIG. 2 illustrates an exemplary imaging system 200 similar to the CT system 100 of FIG. 1. In accordance with aspects of the present disclosure, the imaging system 200 is configured to reconstruct images with a user-specified temporal window in real-time. In one embodiment, the imaging system 200 includes the detector array 108 (see FIG. 1). The detector array 108 further includes a plurality of detector elements 202 that together collect the beams of x-ray radiation 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the CT system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device 216 in the imaging system 200. In one embodiment, image reconstructor 230 may include such instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

As described further herein, the computing device 216 may include computer-readable instructions corresponding to a task-based method for automated tube current modulation (ATCM). This method enables the imaging system 200 to achieve a targeted diagnostic performance for a given clinical protocol and an individual patient (e.g., 95% diagnostic confidence for the detection of liver lesions with size range from 3-10 mm and contrast range from 50-70 HU). In some examples, the method enables individual users (e.g., radiologists) to set up their own preferred image appearance. This is achieved by adjusting and training an optimization model using statistical and machine learning techniques.

More specifically, the system-related information (e.g., system MTF, NPS, pre-specified scanning parameters and so on) and the patient and task-related information (e.g., patient size, clinical task, patient exposure history, and so on) are initially specified as inputs to an ATCM optimization model. A task-related image quality index (denoted herein as $Q_{task}$) is initially determined through a phantom-based approach. The relationship between $Q_{task}$ and dose metrics including volume computed tomography dose index ($CTDI_{vol}$) and size-specific dose estimate (SSDE) is assessed at multiple dose levels to determine the optimized protocol and the dose operating point for the ATCM subsystem. The image quality optimized through such a procedure can then be evaluated by the radiologist to establish an individualized performance/preference curve. A training (for example, neural network) process is further integrated to achieve optimized or preferred diagnostic performance.

Figure 3:
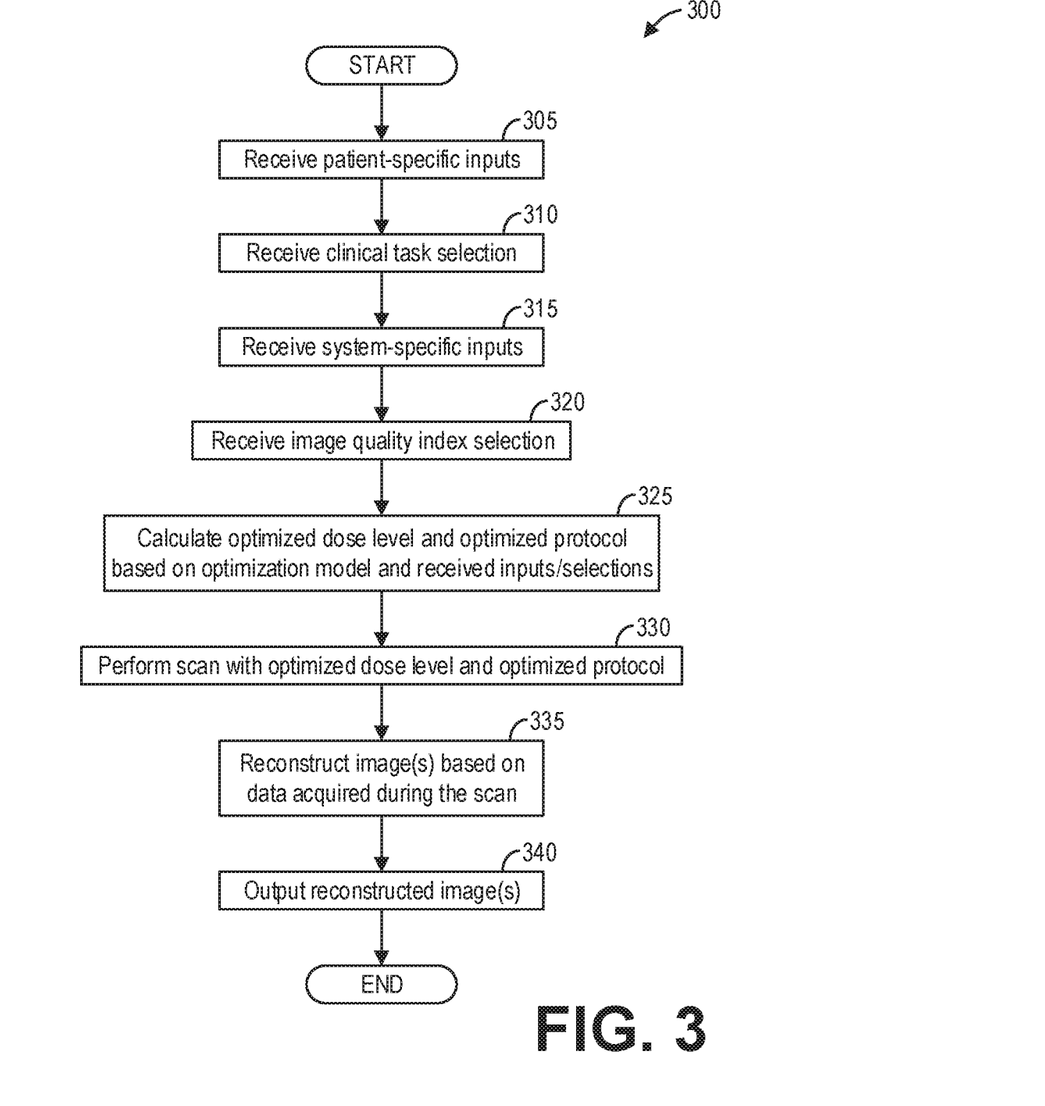
FIG. 3 shows a high-level flow chart illustrating an example method for automatic tube current modulation according to an embodiment of the invention.

FIG. 3 shows a high-level flow chart illustrating an example method 300 for automatic tube current modulation (ATCM) according to an embodiment. In particular, method 300 relates to an optimization model which generates a customized dose level and optimized scan protocol based on a plurality of inputs. The optimization model is updated based on user feedback regarding subjective preferences of image quality. The method will be described with regard to the systems and components described herein with regard to FIGS. 1-2, however it should be understood that the method may be implemented with other systems and components without departing from the scope of the present disclosure.

Method 300 begins at 305. At 305, method 300 receives patient-specific inputs. Patient-specific inputs comprise information describing the patient to be scanned which may be input to the optimization model. To that end, patient-specific inputs may include, but are not limited to, patient size, previous exposure history, and so on. In some examples, the method 300 may automatically determine the patient size, for example, by performing a scout scan of the patient, and calculating the patient size based on projection data acquired during the scout scan. For example, patient size may be expressed in terms of a water-equivalent diameter Dw, which may be calculated based on CT numbers of projection data from the scout scan. Specifically, the water-equivalent diameter Dw is estimated as the diameter of a water-equivalent area, which is calculated as $$D_{area} = \sum \left(\frac{HU}{1000} + 1\right)a,$$

where HU comprises the CT number for each pixel and a comprises the pixel area. Since the region of a patient being scanned may not be uniform in size, the water-equivalent diameter Dw may be calculated for each projection angle. In this way, the dose level may be adapted throughout the region being scanned based on the patient size at each angle. Alternatively, in some examples a single water-equivalent diameter Dw may be used to describe the patient size.

In some examples, the water-equivalent diameter $D_w$ may be estimated without the use of a scout scan. For example, $D_w$ can be estimated by a user with personal experience or from references of suitable body size parameters (e.g., body height and/or weight). It should also be appreciated that in some examples, the patient size may be expressed in terms other than the water-equivalent diameter.

Previous exposure history of the patient may be taken into account when determining radiation dose level. For example, the previous exposure history may provide constraints (e.g., an upper limit) on the dose level, such that patients with large amounts of previous radiation exposure may be presently exposed to lower dose levels than patients with small amounts of previous radiation exposure. Previous exposure history can also be used as a reference to guide the appropriate dose target selection for the patient under study.

After receiving the patient-specific inputs, method 300 continues to 310. At 310, method 300 receives a clinical task selection. Specifically, an operator of the imaging system may select, via a user interface of the imaging system 200, a clinical or diagnostic task which defines the objective of the scan. For example, the clinical task selection may comprise an indication of a task (e.g., detection, screening, and so on). The clinical task selection may further comprise an indication of a targeted contrast level, a targeted lesion size, and so on. For some tasks, spatial resolution may be more important, while for other tasks, the noise may be more important. For some screening tasks, for example, the dose may be more important, as such screenings typically use a low dose. To that end, the method may reference a lookup table containing a set of constraints and/or a standard scan protocol corresponding to the selected clinical task, and such constraints may be applied to the optimization model and/or the standard scan protocol may be adjusted based on the optimization model.

At 315, method 300 receives system-specific inputs. System-specific inputs comprise information describing the particular imaging system 200 which may be input to the optimization model. To that end, system-specific inputs may include the system modulation transfer function (MTF), the system noise power spectrum (NPS), scan parameters, reconstruction parameters, and so on. As a non-limiting example, one or more of the system-specific inputs may be received or retrieved from a lookup table stored within computing device 216. For example, the MTF and/or NPS of the imaging system 200 may be measured and stored within the imaging system 200 (e.g., within the computing device 216). Such characteristics may change over time (e.g., as components of the imaging system 200 are degraded or replaced), and therefore the system characteristics may be periodically measured, in some examples.

As understood in the art, the MTF describes the spatial resolution of the imaging system in the spatial frequency domain. Additionally or alternatively, the point spread function (PSF) may be used to describe the spatial resolution of the imaging system in the spatial domain. Similarly, the NPS describes the noise of the imaging system 200 in the spatial frequency domain, while additionally or alternatively, the standard deviation of the pixel values in the spatial domain may be used to describe the noise of the imaging system 200.

It should further be appreciated that other system-specific image quality parameters, including but not limited to a contrast transfer function (CTF), signal-to-noise ratio (SNR), and contrast-to-noise ratio (CNR), may be measured and thus received at 315 as input to the optimization model.

The scan parameters and reconstruction parameters may include, but are not limited to, kernel, slice thickness, post-processing filters, and so on. Such parameters may be automatically determined (e.g., based on clinical task) or may be manually input or selected by the user (e.g., via a user interface such as operator console 220).

At 320, method 300 receives an image quality index selection. The image quality index selection may comprise a particular value of the image quality index Qtask selected by the user/operator of the imaging system 200. To that end, the user may select, via a user interface such as the operator console 220, a target image quality.

In conventional imaging systems, a single parameter describing noise level (e.g., image pixel standard deviation) is often used as the image quality index in automatic tube current modulation. In contrast, the image quality index $Q_{task}$ utilized in method 300 is based on a plurality of factors which may impact the image quality. For example, with the measurements of physical properties including the contrast, noise, NPS, and MTF, the image quality index $Q_{task}$ may be modeled as a function of these properties:

$$Q_{task} = f(\text{Contrast}, \sigma, \text{MTF}, \text{NPS}),$$

where the noise magnitude σ may be modeled as a function of patient's water-equivalent diameter $D_w$ determined at 305:

$$\sigma = B\sqrt{\exp(uD_w)},$$

where $uD_w$ comprises the inherent attenuation of the scanned object (i.e., the patient), and B is a factor determined by the scanner and scanning parameters. The contrast may be modeled as a function of the tube voltage settings based on a phantom-based study performed with the imaging system. For contrast-enhanced CT examinations, the HU number of both the signal and the background may be explicitly modeled. If such a metric is used for spectral imaging, the contrast may be modeled as a function of keV using a similar approach. As a non-limiting example, the image quality index $Q_{task}$ may be expressed as:

$$Q_{task} = \frac{C \int MTF(u)du}{\sigma * NPS_{peak}^{-1}}.$$

where C is the contrast.

The image quality index $Q_{task}$ may further be modeled as a function of the scanning parameters as:

$$Q_{task} = g(kVp, mAs, \text{slice thickness}, D_w, \text{recon}, \text{kernel}),$$

where kVp is the peak tube kilvoltage, mAs is the current-scan time product, and recon is the reconstruction algorithm. As a non-limiting example, the image quality index $Q_{task}$ may be modeled in the form:

$$Q_{task} = \frac{C_{kV} * MTF_{kernel,recon}}{\frac{1}{\sqrt{mAs}} * \frac{1}{\sqrt{\text{slice thickness}}} * \sqrt{\exp(uD_w)} * NPS_{kernel,recon}},$$

where it should be appreciated that the MTF and the NPS depend on the reconstruction kernel and algorithm while the contrast $C_{kV}$ depends on the tube voltage as described above.

Further, the image quality may be empirically characterized as a function of dose index. For example, a phantom-based study may be performed to measure image quality for a plurality of peak tube kilovoltages at a given water-equivalent diameter. Such a study may further be based on a clinical task. As an illustrative example, FIG. 5 shows a graph 500 illustrating a relationship between image quality levels and dose metrics for different peak tube kilovoltages (kVp). In particular, graph 500 illustrates the image quality metric $Q_{task}$ as a function of $CTDI_{vol}$ levels for patients with a water-equivalent diameter $D_w$ of 24 cm. The measurements are performed at four kVp settings with the clinical task modeled as the detection of liver lesions (e.g., lesion size range 3-10 mm, contrast 4.0 mg/mL). In the depicted example, the measurements 504 are acquired at 80 kVp and the curve 505 is calculated from the measurements 504. Similarly, the measurements 509 are acquired at 100 kVp while the curve 510 is calculated from the measurements 509; the measurements 514 are acquired at 120 kVp while the curve 515 is calculated from the measurements 514; and the measurements 519 are acquired at 140 kVp while the curve 520 is calculated from the measurements 519. It should be appreciated that the image quality-dose index curves may be measured and calculated for many such kVp settings aside from the four depicted in graph 500, as well as a plurality of clinical task settings and water-equivalent diameters. These curves may be obtained prior to performing a diagnostic scan, such that the optimization of dose level and scan protocol as described herein may be based on said curves. For example, such curves can be used to determine the dose operating point for the CT examination at each kVp setting. As described further herein, these curves can assist in the selection of optimal kVp based on the patient size and clinical task.

As another illustrative example of how the image quality index may be correlated to a dose index, FIG. 6 shows a graph 600 illustrating relationships between image quality levels and dose metrics for patients of different sizes. In particular, graph 600 includes a plurality of measurements of the image quality level $Q_{task}$ as a function of the size-specific dose estimate. The plurality of measurements 609 (and the curve 610 derived therefrom) correspond to an average-sized patient, specifically a patient with a water-equivalent diameter $D_w$ of 24 centimeters, while the plurality of measurements 614 (and the curve 615 derived therefrom) correspond to an obese patient, specifically a patient with a water-equivalent diameter $D_w$ of 36 centimeters. In this example, a detection task with contrast level of 30 HU and lesion size of 3-10 mm is selected. As seen in graph 600, a targeted image quality level of 5 corresponds to a much larger SSDE for a larger patient (as depicted by curve 615) than for a smaller patient (as depicted by curve 610).

Referring again to FIG. 3, in view of the above, it should be appreciated that the selection of the image quality index $Q_{task}$ comprises more than a selection of a desired noise level.

Further, while the inputs and selections performed at 305, 310, 315, and 320 are depicted in FIG. 3 as occurring in a specific order, it should be appreciated that the method may receive at least a portion of the selections and inputs in a different order or substantially at the same time (e.g., through submission of a form including two or more of the selections and inputs via the operator console 220).

After receiving the image quality index selection, method 300 continues to 325. At 325, method 300 determines an optimized dose level and an optimized scan protocol based on the optimization model and the received inputs and selections. The dose level may be determined using an image quality-dose index curve such as those described herein above with regard to FIGS. 5-6. Specifically, the image quality-dose index curves may be stored in the form of lookup tables, and the appropriate dose index is determined based on the corresponding image quality index selection. In this way, the optimized dose level is determined based on the image quality index selection, the patient size, and the clinical task.

Furthermore, the method determines the optimized scan protocol based on the image quality models described above. For example, for the desired image quality index and the inputs and selections received at 305, 310, 315, and 320, the method may determine an optimal tube current-time product (mAs).

As an illustrative example, consider a smaller patient with a water-equivalent diameter of 24 centimeters and a larger patient with a water-equivalent diameter of 36 centimeters (which may be determined/input at 305). For a clinical task selection including a target clinical task of detection, a targeted contrast level of 30 HU, and a targeted lesion size of 3-10 millimeters, an operator may select a targeted image quality level of 5. The optimal dose level may be determined based on, for example, the curves 610 and 615 of FIG. 6. Specifically, using the SSDE dose index, an image quality level of 5 corresponds to 7.5 milligray and 32.4 milligray for the smaller and larger patients, respectively. The optimization model (e.g., the $Q_{task}$ formulas described above) may further determine that with a slice thickness of 0.625, the current-time product should be 62.5 mAs and 350 mAs for the smaller and the larger patients, respectively. In some examples, the optimization model may output an optimal slice thickness.

Method 300 proceeds to 330 after determining the optimized dose level and scan protocol. At 330, method 300 performs a scan with the optimized dose level and optimized scan protocol. To that end, the current applied to the x-ray source is varied during the scan. Continuing at 335, method 300 reconstructs one or more images based on data acquired during the scan. The one or more images may be reconstructed using, as non-limiting example, an analytic reconstruction algorithm such as filtered backprojection or an iterative reconstruction algorithm. At 340, method 300 outputs the one or more reconstructed images to a display device such as display device 232. In this way, the operator of the imaging system may review the image(s). Method 300 then ends.

In this way, the targeted image quality index comprehensively models the essential attributes of a diagnostic procedure including the task-related information, the system-related parameters, and the patient-related attributes. Such an image quality index, once correlated with the diagnostic confidence or diagnostic accuracy, enables optimized diagnostic performance for individual patients, clinical tasks, and specific radiologists.

The image quality index $Q_{task}$ described herein incorporates elements of different attributes of image quality using a relatively linear model. However, in actual clinical practice, it is likely that the image quality metrics may not behave in a linear manner due to the variability of clinical imaging tasks, the nonlinear properties of the CT system, and inconsistency across human visual/perceptive systems. Furthermore, individual radiologists may have different preferences regarding the appearance of an image. For example, some radiologists may prefer smooth images, and therefore may typically use a large dose to obtain a smoother image with a better signal-to-noise ratio; meanwhile, other radiologists may prefer sharper images, and so may typically use a different dose and reconstruction method to obtain a sharper image. Such preferences may be captured through user feedback, and training the optimization model, as described herein below with regard to FIG. 4, based on such preferences will adjust the model to reflect these preferences.

A machine learning process can be established using the image quality metric $Q_{task}$ described herein above with regard to FIG. 3 as an initial model. As a non-limiting example, each scanning parameter (including mAs, kVp, slice thickness, contrast injection, reconstruction algorithm, and reconstruction kernel) can be modeled as the training parameters. The radiologists evaluate the image appearance in terms of the overall image quality acceptance and diagnostic confidence. The evaluation can be used to accommodate the perception performance and adjust the image quality-dose curve, for example. Furthermore, the large clinical image database acquired from the daily clinical practice at an individual institute can be used as training data to achieve optimized image quality for the individual radiologist and the clinical institution.

FIG. 4 shows a high-level flow chart illustrating an example method 400 for adapting an optimization model based on user feedback. In particular, method 400 relates to obtaining user feedback regarding the quality of an image, and using this user feedback to train or adjust the optimization model used to generate the image. Method 400 may be performed, for example, after an image is displayed to an operator (e.g., after 335 in method 300). The method 400 will be described with regard to the systems and components described herein with regard to FIGS. 1-2, as well as the method described herein with regard to FIG. 3, however it should be understood that the method 400 may be implemented with other systems, components, and methods without departing from the scope of the present disclosure.

Method 400 begins at 405. At 405, method 400 outputs an image quality assessment survey to a display device, such as display device 232, for display to a user. The image quality assessment survey includes one or more questions regarding the quality of an image generated in accordance with a method for automated tube current modulation, such as method 300. The one or more questions may be provided to determine the user's diagnostic confidence regarding the image, whether the user believes the perceived image quality corresponds to the selected image quality, whether the image should be more or less sharp, whether the image should be more or less smooth, and so on.

At 410, method 400 receives user feedback for the image quality assessment survey. The user may input responses to the image quality assessment survey using a user interface, such as operator console 220, and thus the method may receive the user feedback comprising the responses from the user interface. The user feedback may be qualitative and/or quantitative. However, for the purpose of updating the optimization model using a machine learning algorithm as described further herein, preferably the user feedback is quantitative (i.e., numerical) in nature. To that end, in examples where at least some of the user feedback is qualitative, the qualitative responses may be converted to a numerical format.

At 415, method 400 updates the optimization model based on the user feedback. To update the optimization model, the method may use one or more machine learning algorithms. Specifically, in some examples, the method may use a nonlinear statistical data modeling technique such as a neural network. For example, the neural network may take the initial optimization model (i.e., the optimization model described herein above with regard to FIG. 3) and tune the optimization model based on the user feedback. The user feedback regarding the image and all of the relevant parameters used to generate the image (including but not limited to the patient-specific inputs, the system-specific inputs, the clinical task selection, the image quality selection, the optimized dose level, the optimized scan protocol, and so on) may be used as input features for the neural network. The neural network then adjusts the optimization model based on these input features. In this way, as more images are created and more user feedback regarding those images is received over time, the optimization model becomes personalized to the particular imaging system as well as the subjective preferences of one or more users (e.g., radiologists).

In some examples the optimization model may be trained based on images previously generated according to method 300 as well as user feedback regarding the quality of the previously-generated images. Specifically, the initial optimization model described above may be used as an initial function for a neural network or another machine learning algorithm, which then updates the model based on the user feedback. Consequently, the particular optimization model used to determine the dose level and scan protocol at 325 may comprise a trained optimization model. In some examples, the imaging system may include one or more optimization models corresponding to different users of the imaging system. In such examples, the optimization model corresponding to the particular user of the imaging system may be used to determine the dose level and scan protocol to reflect previously-received user feedback regarding image quality. To that end, users of the imaging system may establish a user profile on the computer, and adjustments to the optimization model may be saved to a user's user profile. Prior to performing a scan, the user may load their user profile including the adjusted optimization model such that the execution of method 300, for example, may use the adjusted optimization model rather than an initial optimization model. In some examples, the imaging system may only include one such user profile that is accessed and updated by all users of the imaging system.

While neural networks are described herein, it should be appreciated that any appropriate supervised machine learning technique may be utilized to train the optimization model. Method 400 ends after updating the optimization model.

A technical effect of the disclosure includes the modulation of tube current applied to an x-ray source while scanning an object, wherein the modulation is based on the clinical task, the physical characteristics of the object, and the physical characteristics of the imaging system. Another technical effect is the reconstruction and display of an image with a desired image quality. Yet another technical effect of the disclosure is the calculation of an optimal dose level and scan protocol to achieve a targeted image quality, and the scanning of an object according to the optimal dose level and scan protocol.

Various systems and methods for automated tube current modulation are provided. In one embodiment, a method for an imaging system comprises: calculating a desired dose level based on a clinical task, a size of a subject to be scanned, and an image quality level; generating a scan protocol based on a relation between the image quality level and at least one characteristic of the imaging system; and performing a scan of the subject at the desired dose level and according to the scan protocol.

In a first example of the method, the image quality level and the clinical task are selected by a user of the imaging system. In a second example of the method optionally including the first example, the method further comprises performing a scout scan of the subject, and calculating the size of the subject based on data acquired during the scout scan. In a third example of the method optionally including one or more of the first and second examples, the at least one characteristic of the imaging system comprises one or more of a modulation transfer function and a noise power spectrum. In a fourth example of the method optionally including one or more of the first through third examples, the method further comprises reconstructing an image based on data acquired during the scan, and outputting the image to a display device. In a fifth example of the method optionally including one or more of the first through fourth examples, the method further comprises outputting an image quality assessment survey to the display device, the image quality assessment survey comprising at least one question regarding image quality of the reconstructed image, and receiving user feedback for the image quality assessment survey, the user feedback comprising a response to the at least one question provided by a user of the imaging system via a user interface of the imaging system. In a sixth example of the method optionally including one or more of the first through fifth examples, the method further comprises updating the optimization model based on the user feedback. In a seventh example of the method optionally including one or more of the first through sixth examples, updating the relation based on the user feedback comprises adjusting the relation with a neural network, wherein the user feedback and one or more of the clinical task, the image quality level, the size of the subject, the optimized dose level, the scan protocol, the at least one characteristic of the imaging system, the reconstructed image, and combinations thereof comprise inputs to the neural network. In an eighth example of the method optionally including one or more of the first through seventh examples, the updated relation is associated with the user, and the method further comprises performing a subsequent scan according to a second scan protocol generated based on the updated relation when the user is operating the imaging system. In a ninth example of the method optionally including one or more of the first through eighth examples, the scan protocol comprises a tube current-time product. In a tenth example of the method optionally including one or more of the first through ninth examples, calculating the desired dose level based on the clinical task, the size of the subject, and the image quality level comprises: accessing a table corresponding to the clinical task and the size of the subject, the table including a plurality of pairs of dose levels and image quality levels; and retrieving the desired dose level corresponding to the image quality level.

In another embodiment, a non-transitory computer-readable storage medium includes executable instructions stored thereon that when executed by a computer cause the computer to: determine a dose level and a scan protocol based on physical characteristics of a subject to be scanned, physical characteristics of an x-ray source and a detector communicatively coupled to the computer, a clinical task, and a relationship therebetween; perform, with the x-ray source and the detector, a scan of the subject with the dose level and the scan protocol; output, to a display device communicatively coupled to the computer, an image reconstructed from data acquired during the scan; receive, from a user interface communicatively coupled to the computer, user feedback regarding quality of the image; and adjust the relationship based on the user feedback, the physical characteristics of the subject, the physical characteristics of the x-ray source and the detector, and the clinical task.

In a first example of the non-transitory computer-readable storage medium, adjusting the relationship comprises training a neural network with the relationship, the user feedback, the physical characteristics of the subject, the physical characteristics of the x-ray source and the detector, and the clinical task. In a second example of the non-transitory computer-readable storage medium optionally including the first example, the executable instructions further cause the computer to save the adjusted relationship to a user profile, and perform a subsequent scan with a dose level and a scan protocol determined based on the adjusted relationship responsive to a selection of the user profile. In a third example of the non-transitory computer-readable storage medium optionally including one or more of the first and second examples, the physical characteristics of the subject comprise one or more of a size of the subject and an exposure history of the subject, and the physical characteristics of the x-ray source and the detector comprise one or more of a modulation transfer function and a noise power spectrum.

In yet another embodiment, an imaging system comprises: an x-ray source that emits a beam of x-rays toward an object to be imaged; a detector that receives the x-rays attenuated by the object; a data acquisition system (DAS) operably connected to the detector; and a computer operably connected to the DAS and configured with instructions in non-transitory memory that when executed cause the computer to: calculate a target dose level based on a clinical task, a size of the object, and an image quality level; generate a scan protocol based on an optimization model comprising a relation between the image quality level and at least one physical characteristic of the imaging system; and perform, with the x-ray source and the detector, a scan of the object at the target dose level and according to the scan protocol.

In a first example of the imaging system, the imaging system further comprises a display device communicatively coupled to the computer, and the computer is further configured with instructions in the non-transitory memory that when executed cause the computer to reconstruct an image based on data received from the DAS during the scan, and output the image to the display device. In a second example of the imaging system optionally including the first example, the imaging system further comprises a user interface communicatively coupled to the computer, and the instructions further cause the computer to output an image quality survey to the display device, receive responses to the image quality survey provided by a user of the imaging system via the user interface, and adjust the optimization model based on the responses. In a third example of the imaging system optionally including one or more of the first and second examples, adjusting the optimization model based on the responses comprises training a machine learning algorithm with one or more of the responses, the at least one physical characteristic of the imaging system, the clinical task, the image quality level, the size of the subject, the scan protocol, and the target dose level. In a fourth example of the imaging system optionally including one or more of the first through third examples, the machine learning algorithm may comprise a neural network. In a fifth example of the imaging system optionally including one or more of the first through fourth examples, performing the scan according to the scan protocol comprises varying a current applied to the x-ray source based on the size of the object.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
   calculating a desired dose level based on a clinical task, a size of a subject to be scanned, and an image quality level;
   generating a scan protocol based on a relation between the image quality level and at least one physical characteristic of the imaging system; and
   performing a scan of the subject at the desired dose level and according to the generated scan protocol.

2. The method of claim 1, further comprising selecting the image quality level and the clinical task by a user of the imaging system.

3. The method of claim 1, further comprising performing one or more scout scans of the subject, and calculating the size and a shape of the subject based on data acquired during the one or more scout scans.

4. The method of claim 1, wherein the at least one physical characteristic of the imaging system comprises one or more of a modulation transfer function and a noise power spectrum.

5. The method of claim 1, further comprising reconstructing an image based on data acquired during the scan, and outputting the image to a display device.

6. The method of claim 5, further comprising:
   outputting an image quality assessment survey to the display device, the image quality assessment survey comprising at least one question regarding image quality of the reconstructed image; and
   receiving user feedback for the image quality assessment survey, the user feedback comprising a response to the at least one question provided by a user of the imaging system via a user interface of the imaging system.

7. The method of claim 6, further comprising updating the relation based on the user feedback.

8. The method of claim 7, wherein updating the relation based on the user feedback comprises adjusting the relation with a machine learning algorithm, wherein the user feedback and one or more of the clinical task, the image quality level, the size of the subject, the desired dose level, the generated scan protocol, the at least one physical characteristic of the imaging system, the reconstructed image, and combinations thereof comprise inputs to a neural network.

9. The method of claim 7, wherein the updated relation is associated with the user, and further comprising performing a subsequent scan according to a second scan protocol generated based on the updated relation when the user is operating the imaging system.

10. The method of claim 1, wherein the generated scan protocol comprises a tube current-time product.

11. The method of claim 1, wherein calculating the desired dose level based on the clinical task, the size of the subject, and the image quality level comprises:
    accessing a table corresponding to the clinical task and the size of the subject, the table including a plurality of pairs of dose levels and image quality levels; and
    retrieving from the table the desired dose level corresponding to the image quality level.

12. A non-transitory computer-readable storage medium including executable instructions stored thereon that when executed by a computer cause the computer to:
    determine a dose level and a scan protocol based on physical characteristics of a subject to be scanned, physical characteristics of an x-ray source and a detector communicatively coupled to the computer, a clinical task, and a relationship there between;
    perform, with the x-ray source and the detector, a scan of the subject with the dose level and the scan protocol;
    output, to a display device communicatively coupled to the computer, an image reconstructed from data acquired during the scan;
    receive, from a user interface communicatively coupled to the computer, user feedback regarding quality of the image; and
    adjust the relationship based on the user feedback, the physical characteristics of the subject, the physical characteristics of the x-ray source and the detector, and the clinical task.

13. The non-transitory computer-readable storage medium of claim 12, wherein the executable instructions cause the computer to adjust the relationship by training a neural network with the relationship, the user feedback, the physical characteristics of the subject, the physical characteristics of the x-ray source and the detector, and the clinical task.

14. The non-transitory computer-readable storage medium of claim 12, wherein the executable instructions further cause the computer to save the adjusted relationship to a user profile, and perform a subsequent scan with a dose level and a scan protocol determined based on the adjusted relationship responsive to a selection of the user profile.

15. The non-transitory computer-readable storage medium of claim 12, wherein the physical characteristics of the subject comprise one or more of a size of the subject and an exposure history of the subject, and wherein the physical characteristics of the x-ray source and the detector comprise one or more of a modulation transfer function and a noise power spectrum.

16. An imaging system, comprising:
    an x-ray source that emits a beam of x-rays toward a subject to be imaged;
    a detector that receives the beam of x-rays attenuated by the subject;
    a data acquisition system (DAS) operably connected to the detector; and
    a computer comprising non-transitory memory and operably connected to the DAS, wherein the computer is configured with instructions in the non-transitory memory that when executed cause the computer to:
- calculate a desired dose level based on a clinical task, a size of the subject, and an image quality level;
- generate a scan protocol based on an optimization model comprising a relation between the image quality level and at least one physical characteristic of the imaging system; and
- perform, with the x-ray source and the detector, a scan of the subject at the desired dose level and according to the scan protocol.

17. The imaging system of claim 16, further comprising a display device communicatively coupled to the computer, wherein the computer is further configured with instructions in the non-transitory memory that when executed cause the computer to reconstruct an image based on data received from the DAS during the scan, and output the image to the display device.

18. The imaging system of claim 17, further comprising a user interface communicatively coupled to the computer, wherein the instructions further cause the computer to output an image quality survey to the display device, receive responses to the image quality survey provided by a user of the imaging system via the user interface, and adjust the optimization model based on the responses.

19. The imaging system of claim 18, wherein adjusting the optimization model based on the responses comprises training a neural network with one or more of the responses, the at least one physical characteristic of the imaging system, the clinical task, the image quality level, the size of the subject, the scan protocol, and the desired dose level.

20. The imaging system of claim 16, wherein performing the scan according to the scan protocol comprises varying a current applied to the x-ray source based on the size of the subject.

* * * * *